United States Patent
Von Arx et al.

(10) Patent No.: US 7,831,828 B2
(45) Date of Patent: Nov. 9, 2010

(54) SYSTEM AND METHOD FOR SECURELY AUTHENTICATING A DATA EXCHANGE SESSION WITH AN IMPLANTABLE MEDICAL DEVICE

(75) Inventors: Jeffrey A. Von Arx, Minneapolis, MN (US); Scott J. Healy, Maple Grove, MN (US); Scott Vanderlinde, Plymouth, MN (US)

(73) Assignee: Cardiac Pacemakers, Inc. MN (US)

( * ) Notice: Subject to any disclaimer, the term of this patent is extended or adjusted under 35 U.S.C. 154(b) by 1076 days.

(21) Appl. No.: 10/800,806

(22) Filed: Mar. 15, 2004

(65) Prior Publication Data

US 2005/0204134 A1 Sep. 15, 2005

(51) Int. Cl.
H04L 9/32 (2006.01)
A61N 1/00 (2006.01)

(52) U.S. Cl. ............... 713/169; 713/168; 713/171; 713/172; 713/173; 713/174; 713/175; 607/31; 607/60

(58) Field of Classification Search ......... 713/168–175; 607/31, 60
See application file for complete search history.

(56) References Cited

U.S. PATENT DOCUMENTS

| | | | |
|---|---|---|---|
| 4,562,841 A | 1/1986 | Brockway et al. | |
| 5,113,869 A | 5/1992 | Nappholz et al. | |
| 5,720,770 A | 2/1998 | Nappholz et al. | |
| 5,752,976 A | 5/1998 | Duffin et al. | |
| 5,887,063 A | 3/1999 | Varadharajan et al. | |
| 6,024,699 A | 2/2000 | Surwit et al. | |
| 6,083,248 A | 7/2000 | Thompson | |
| 6,171,256 B1 | 1/2001 | Joo et al. | |
| 6,298,271 B1 * | 10/2001 | Weijand | 607/60 |
| 6,416,471 B1 | 7/2002 | Kumar et al. | |
| 6,434,429 B1 | 8/2002 | Kraus et al. | |
| 6,456,256 B1 | 9/2002 | Amundson et al. | |
| 6,564,104 B2 | 5/2003 | Nelson et al. | |
| 6,574,510 B2 | 6/2003 | Von Arx et al. | |
| 6,614,406 B2 | 9/2003 | Amundson et al. | |
| 6,827,670 B1 | 12/2004 | Stark et al. | |
| 7,039,810 B1 * | 5/2006 | Nichols | 713/182 |

(Continued)

FOREIGN PATENT DOCUMENTS

EP 0 756 397 1/1997

(Continued)

OTHER PUBLICATIONS

Microsoft® Computer Dictionary, Fifth Edition by Microsoft Corporation Pub Date: May 1, 2002 Excerpt: server.*

(Continued)

Primary Examiner—Kambiz Zand
Assistant Examiner—Benjamin A Kaplan
(74) Attorney, Agent, or Firm—Pauly, DeVries Smith & Deffner. L.L.C.

(57) ABSTRACT

A system and method for securely authenticating a data exchange session with an implantable medical device is presented. A crypto key uniquely associated with an implantable medical device is defined to authenticate data during a data exchange session. A secure connection is established from an external source with a secure key repository securely maintaining the crypto key. Authorization to access data on the implantable medical device is authenticated by securely retrieving the crypto key from the secure key repository.

10 Claims, 11 Drawing Sheets

U.S. PATENT DOCUMENTS

| | | | |
|---|---|---|---|
| 7,136,999 B1* | 11/2006 | Griffiths | 713/168 |
| 7,155,290 B2* | 12/2006 | Von Arx et al. | 607/60 |
| 7,228,182 B2* | 6/2007 | Healy et al. | 607/60 |
| 7,475,245 B1 | 1/2009 | Healy et al. | |
| 2001/0027331 A1 | 10/2001 | Thompson | |
| 2001/0039504 A1* | 11/2001 | Linberg et al. | 705/3 |
| 2002/0016913 A1* | 2/2002 | Wheeler et al. | 713/170 |
| 2002/0065099 A1 | 5/2002 | Bjorndahl | |
| 2002/0095507 A1* | 7/2002 | Jerdonek | 709/229 |
| 2003/0114897 A1 | 6/2003 | Von Arx et al. | |
| 2004/0260363 A1* | 12/2004 | Arx et al. | 607/60 |
| 2005/0262418 A1* | 11/2005 | Gehrmann | 714/758 |
| 2007/0118188 A1 | 5/2007 | Von Arx et al. | |

FOREIGN PATENT DOCUMENTS

| | | |
|---|---|---|
| EP | 0756397 | 1/1997 |
| WO | WO-98/59327 | 12/1998 |
| WO | WO-99/41876 | 8/1999 |
| WO | WO-03/008037 A2 | 1/2003 |
| WO | WO-2005/000397 | 1/2005 |

OTHER PUBLICATIONS

B. Schneier, "Applied Cryptography, Second Edition," Applied Cryptography. Protocols, Algorithms, and Source Code Inc., John Wiley & Sons, p. 31-42 (1996).

Health Insurance Portability And Accountability Act of 1996, Pub. L. No. 104-191, 110 Stat. 1936 (1996).

W. Diffie, "The First Ten Years of Public-Key Cryptography," Proceedings of the IEEE, vol. 76, No. 5, pp. 560-577 (May 1988).

E. Hammond, "National Committee On Vital and Health Statistics, Subcommittee on Health Data Needs, Standards and Security," http://www.ncvhs.hhs.gov/970211t3.htm, pp. 1-4 (Feb. 11, 1997).

Security And Electronics Signature Standards, 63 Fed. Reg. 155 (proposed Aug. 12, 1998) (to be codified at 45 C.F.R. pt. 142).

European Search Report and Written Opinion for EP Patent Application No. 05725671, dated Apr. 19, 2002, and May 2, 2002 (6 pages).

File history for EP 05725671.1, filed Mar. 15, 2005 (191 pages).

International Preliminary Report on Patentability for PCT/US2005/008650, received Oct. 5, 2006, and Written Opinion of the International Searching Authority, Dec. 15, 2005 (11 pages).

Menezes et al. "Handbook of Applied Cryptography, Challenge-Response Identification (Strong Authentication)" Handbook of Applied Cryptography, CRC Press Series on Discrete Mathematics and its Applications, Boca Raton, FL, CRC Press, US, 1997, pp. 397-405.

Translation of Office Action for Japanese Patent Application No. 2007-504044 from the Japanese Patent Office, dated Sep. 16, 2009 (4 pages).

* cited by examiner

120

230

240

260

SYSTEM AND METHOD FOR SECURELY AUTHENTICATING A DATA EXCHANGE SESSION WITH AN IMPLANTABLE MEDICAL DEVICE

FIELD OF THE INVENTION

The present invention relates in general to data exchange session authentication and, specifically, to a system and method for securely authenticating a data exchange session with an implantable medical device.

BACKGROUND OF THE INVENTION

Heart diseases refer to several classes of cardio and cardiovascular disorders and co-morbidities relating to the heart and blood vessels. Heart disease is often treated through a combination of medication and lifestyle modification. In severe cases, a monitoring or therapy delivery device, referred to as an implantable medical device (IMD), is surgically implanted to collect cardiac performance data and to deliver therapy to the heart, when needed. IMDs are also used to provide neural stimulation, dispense drugs, and other functions, as would be appreciated by one skilled in the art.

Periodically, data collected by an IMD can be downloaded for further analysis and, if required, new performance instructions can be uploaded to reprogram the IMD. Typically, an IMD communicates with a programmer or a dedicated repeater located outside the body in a data exchange session. To minimize patient risk, wireless telemetry, such as inductive telemetry, is normally used to non-invasively communicate with the IMD.

Although inductive telemetry requires little or no on-board energy to transmit information, inductive telemetry has a few shortcomings. First, inductive telemetry is short range, typically about six centimeters, and requires close proximity between a patient and the programmer or repeater. The patient's movements are limited while data transfer is ongoing. In addition, inductive telemetry has a slow data transfer rate, which is directly proportional to the carrier signal frequency. Only low frequency signals can be used as carrier signals due to the low-pass filtering effect of the metal casing of the IMD, resulting in a transmission speed of several kilobits per second. This transfer rate is inadequate for modern IMDs, which normally can contain millions of bits of patient physiological data.

Recently, radio frequency (RF) telemetry, a form of long range telemetry, has emerged as a viable alternative to inductive telemetry, such as described in commonly-assigned U.S. Pat. No. 6,456,256, issued Sep. 24, 2002, to Amundson et al.; U.S. Pat. No. 6,574,510, to Von Arx et al., issued Jun. 3, 2003; and U.S. Pat. No. 6,614,406, issued Sep. 2, 2003, to Amundson et al., the disclosures of which are incorporated by reference. Unlike inductive telemetry, RF telemetry is long range, extending to about 20 or more feet from a patient without using repeaters. This range allows a patient free movement while the IMD is accessed. RF telemetry also offers a higher data transfer rate that can significantly shorten download time.

Although promising, the use of RF telemetry in IMDs potentially raises serious privacy and safety concerns. Sensitive information, such as patient-identifiable health information, exchanged between an IMD and the programmer or repeater should be safeguarded to protect against compromise. Prior to initiating a data exchange session, a clinician preferably first informs the patient and then proceeds only with the patient's knowledge. The short range of inductive telemetry can imply informed consent, but the longer range of RF telemetry can require additional precautions to secure proper patient/clinician authentication. Similarly, the wider transmission radius of RF telemetry could allow a third party to monitor or interfere with a data exchange session without authorization. Finally, a data exchange session could mistakenly be conducted with a wrong patient.

Recently enacted medical information privacy laws, including the Health Insurance Portability and Accountability Act (HIPAA) and the European Privacy Directive underscore the importance of safeguarding a patient's privacy and safety and require the protection of all patient-identifiable health information (PHI). Under HIPAA, PHI is defined as individually identifiable health information, including identifiable demographic and other information relating to the past, present or future physical or mental health or condition of an individual, or the provision or payment of health care to an individual that is created or received by a health care provider, health plan, employer or health care clearinghouse. Other types of sensitive information in addition to or in lieu of PHI could also be protectable.

The sweeping scope of medical information privacy laws, such as HIPAA, may affect patient privacy on IMDs with longer transmission ranges, such as provided through RF telemetry, and other unsecured data interfaces providing sensitive information exchange under conditions that could allow eavesdropping, interception or interference. Sensitive information should be encrypted prior to long range transmission. Currently available data authentication techniques for IMDs can satisfactorily safeguard sensitive information. These techniques generally require crypto keys, which are needed by both a sender and recipient to respectively encrypt and decrypt sensitive information transmitted during a data exchange session. Crypto keys can be used to authenticate commands, check data integrity and, optionally, encrypt sensitive information, including any PHI, during a data exchange session. Preferably, the crypto key is unique to each IMD. However, authentication can only provide adequate patient data security if the identification of the crypto key from the IMD to the programmer or repeater is also properly safeguarded.

Therefore, there is a need for a system and method to ensure patient privacy and safety by using secure methods for crypto key exchange. Preferably, such an approach will secure clinician/patient authentication prior to data exchange session initiation and will facilitate transacting a secure crypto key exchange between an IMD and a programmer, repeater or similar device.

SUMMARY OF THE INVENTION

Prior to commencing a data exchange session between an implanted IMD and an external source capable of long range telemetry, such as provided by an RF programmer, repeater or wireless computing device, patient/clinician authentication must be completed, during which a crypto key is identified and retrieved for use during the data exchange session. The crypto key is maintained on a secure key repository and can be used to authenticate individual commands, check data integrity, and, optionally, encrypt sensitive information, including any PHI, or a combination of the foregoing, when transmitted over a long range telemetric link. The crypto key can be either pre-programmed and persistently stored on the IMD, or can be dynamically generated on the IMD, programmer or dedicated repeater. The crypto key is retrieved from the source of the crypto key based on the form of the key and the type of device maintaining the crypto key. For instance, if the crypto key is stored in the IMD, the programmer retrieves the crypto key through inductive telemetry. If the crypto key is maintained in a secure database, the programmer obtains the crypto key through a secure connection to a secure server servicing the secure database. If the crypto key is provided on a physical token, the programmer includes the means for accessing the crypto key from the physical token, such as through optical, magnetic, or serial communication interfaces. Following successful authentication, the external source and the implantable medical device transact a data exchange session by transitioning to long range telemetry.

An embodiment provides a system and method for securely authenticating a data exchange session with an implantable medical device. A crypto key uniquely associated with an implantable medical device is defined to authenticate data during a data exchange session. A secure connection is established from an external source with a secure key repository securely maintaining the crypto key. Authorization to access data on the implantable medical device is authenticated by securely retrieving the crypto key from the secure key repository.

A further embodiment provides a system and method for securely transacting a data exchange session with an implantable medical device. Communication with an implantable medical device is authenticated by authenticating access to a securely maintained crypto key using a short range interface. A data exchange session is commenced by transitioning to long range interface upon successful access authentication with the implantable medical device. The data exchange session is transacted by accessing patient health information stored on the implantable medical device using the crypto key.

Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Implantable Medical Device

Figure 1:
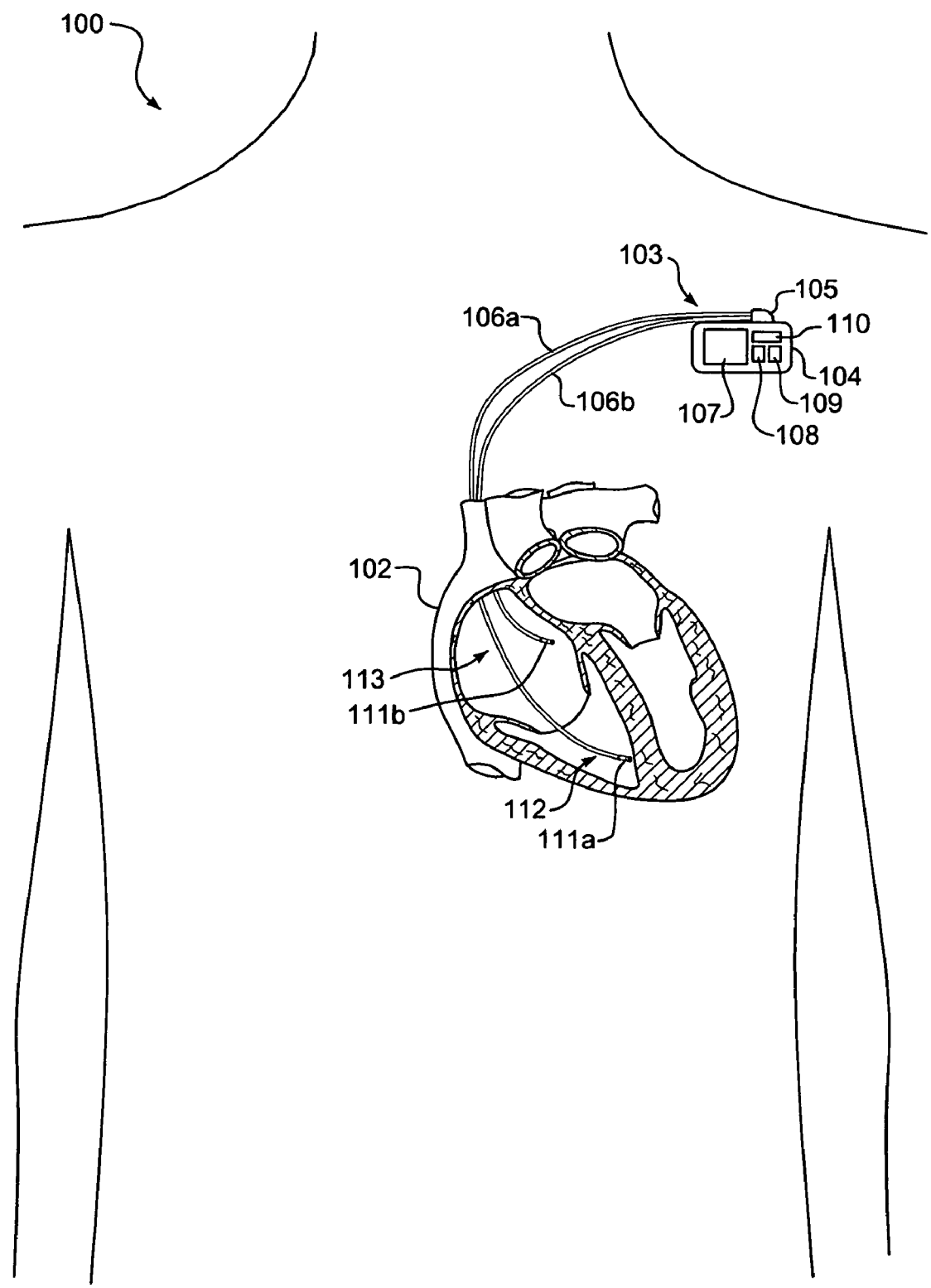
FIG. 1 is a block diagram showing, by way of example, an implantable medical device monitoring physiological parameters of a patient, in accordance with an embodiment of the present invention.

FIG. 1 is a block diagram 100 showing, by way of example, an implantable medical device (IMD) 103 monitoring physiological parameters of a patient, in accordance with an embodiment of the present invention. The IMD 103 is surgically implanted in the chest or abdomen of a patient and consists generally of a housing 104 and terminal block 105. The IMD 103 is coupled to a set of leads 106a-b at the terminal block 105. During surgery, the leads 106a-b are threaded through a vein and placed into the heart 102 with the distal tips of each lead 106a-b positioned in direct contact with tissue inside the heart 102.

The housing 104 contains a battery 107, control circuitry 108, memory 109, and telemetry circuitry 110. The battery 107 provides a finite power source for the IMD components. The control circuitry 108 samples and processes raw data signals and includes signal filters and amplifiers, memory and a microprocessor-based controller. The memory 109 includes a memory store in which raw physiological signals can be stored for later retrieval and analysis. The telemetry circuitry 110 provides an interface between the IMD 103 and external devices, such as a programmer or dedicated repeater (not shown). The telemetry circuitry 110 enables operating parameters to be non-invasively programmed into the memory 109 through an external device in telemetric communication with the IMD 103. The telemetry circuitry 110 also allows patient information collected by the IMD 103 and transiently stored in the memory 109 to be sent to the external device for processing and analysis.

The IMD 103 is in direct electrical communication with the heart 102 through electrodes 111a-b positioned on the distal tips of each lead 106a-b. By way of example, the set of leads 106a-b can include a right ventricular electrode 111a and a right atrial electrode 111b. The right ventricular electrode 111a is preferably placed in the right ventricular apex 112 of the heart 102 and the right atrial electrodes 111b is preferably placed in the right atrial chamber 113 of the heart 102. The electrodes 111a-b enable the IMD 103 to directly collect raw physiological measures, preferably through millivolt measurements. Other configurations and arrangements of leads and electrodes, including the use of single and multiple leads arrays and single and multiple electrodes, can be used, as would be recognized by one skilled in the art.

In the described embodiment, the IMD 103 can be implemented as part of cardiac pacemakers used for managing bradycardia, implantable cardioverter defibrillators (IMDs) used for treating tachycardia, and other types of implantable cardiovascular monitors and therapeutic devices used for monitoring and treating structural problems of the heart, such as congestive heart failure, as well as rhythm problems, as would be appreciated by one skilled in the art. Examples of cardiac pacemakers suitable for use in the described embodiment include the Pulsar Max II, Discovery, and Discovery II pacing systems, sold by Guidant Corporation, St. Paul, Minn. An example of an IMD suitable for use in the described embodiment includes the Contak Renewal cardiac resynchronization therapy defibrillator, also sold by Guidant Corporation, St. Paul, Minn.

On a regular basis, the raw physiological signals stored in the memory 109 are retrieved. By way of example, a programmer or repeater (not shown) can be used to retrieve the raw physiological signals. However, any form of programmer, repeater, interrogator, recorder, monitor, or transceiver suitable for communicating with IMD 103 could be used. In addition, a server, personal computer or digital data processor could be interfaced to the IMD 103, either directly or via a transceiver configured to communicate with the implantable medical device 103.

For short range data exchange, the IMD 103 communicates with the programmer or repeater through inductive telemetry signals exchanged through a wand placed over the location of the IMD 103. Programming or interrogating instructions are sent to the IMD 103 and the stored raw physiological signals are downloaded into the programmer. For long range data exchange, the IMD 103 communicates with an external device capable of long range telemetry, such as a radio frequency (RF) programmer, repeater or other wireless computing device. Other types of data interfaces are possible, as would be appreciated by one skilled in the art. Prior to initiating the long range data exchange session, patient/clinician authentication is performed through secure crypto key 122 retrieval, as further described below with reference to FIG. 2.

In a further embodiment, the IMD 103 includes a telemetry interlock that limits communication between the IMD 103 and an external device. Patient/clinician authentication is secured through release of the telemetry interlock, which can be used in conjunction with secure crypto key 122 retrieval. The telemetry interlock is released when the external device transmits an ENABLE command to the IMD 103 via short range telemetry, such as described in commonly-assigned U.S. Pat. No. 7,155,290 to Von Arx, et al., issued Dec. 26, 2006, the disclosure of which is incorporated by reference.

An example of a programmer with inductive telemetry is the Model 2920 Programmer Recorder Monitor, manufactured by Guidant Corporation, Indianapolis, Ind., which includes the capability to store retrieved raw physiological signals on a removable floppy diskette. The raw physiological signals could later be electronically transferred using a personal computer or similar processing device.

Other alternate raw physiological signals transfer means could also be employed. For instance, the stored raw physiological signals could be retrieved from the IMD 103 and electronically transferred to a network using a combination of a remote external programmer and analyzer and a remote telephonic communicator, such as described in U.S. Pat. No. 5,113,869, to Nappholz et al., issued May 19, 1992, the disclosure of which is incorporated by reference. Similarly, the stored raw physiological signals could be retrieved and remotely downloaded to a server using a world-wide patient location and data telemetry system, such as described in U.S. Pat. No. 5,752,976, to Duffin et al., issued May 19, 1998, the disclosure of which is incorporated by reference.

Although described with reference to implantable cardiac monitoring and therapy delivery, IMDs also include neural stimulation, drug dispensing, and other implantable, as well as external, monitoring and therapy delivery devices, as would be appreciated by one skilled in the art.

Crypto Key Generation and Authentication Process Flow

Figure 2:
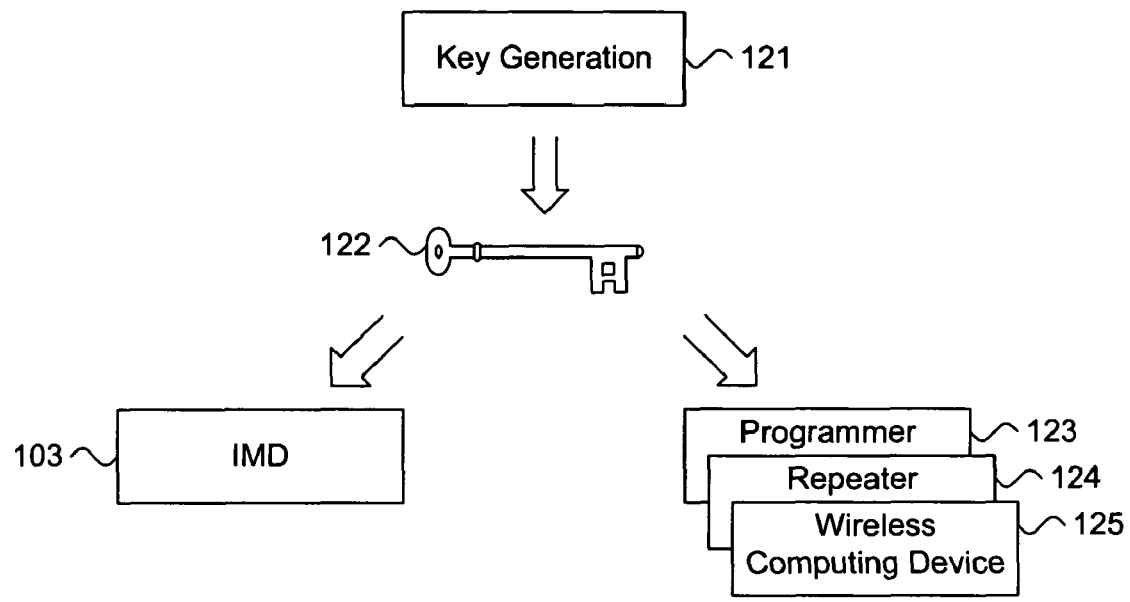
FIG. 2 is a process flow diagram showing crypto key generation and authentication.

FIG. 2 is a process flow diagram 120 showing crypto key generation and authentication. During a data exchange session, sensitive information, including any PHI, is exchanged through RF or other forms of long range telemetry between the IMD 103 and an external source, such as a programmer 123, repeater 124 or other wireless computing device 125. The data exchange session could also be transacted over other types of unsecured data interfaces, as would be appreciated by one skilled in the art. However, prior to initiating the data exchange session over any such unsecured interface, patient/clinician authentication must be secured. Patient/clinician authentication, or simply "authentication," involves an affirmative interaction between a patient and a clinician during which the clinician informs the patient, either directly or by implication, and secures authorization to access the patient information maintained in the IMD 103 and, if necessary, to interrogate and reprogram the IMD 103. Authentication ensures that a clinician does not accidentally start a data exchange session with the wrong patient or without a patient's knowledge. Authentication also provides an opportunity to securely obtain the crypto key 122 uniquely associated with the IMD 103.

Authentication can be completed using statically generated and persistently stored crypto keys, dynamically generated and persistently stored crypto keys, dynamically generated and non-persistently stored session crypto keys, or a combination of the foregoing. Persistently stored crypto keys 122 are maintained in a fixed secure key repository, such as a programmer, patient designator, secure database, token, or repeater, and on the IMD itself. Statically generated and persistently stored crypto keys are stored in the IMD 103 prior to implantation, such as during the manufacturing process. Dynamically generated and persistently stored crypto keys are generated dynamically, such as by a programmer 123 for subsequent download to the IMD 103 using short range telemetry following implantation. Dynamically generated and non-persistently stored session crypto keys are also generated dynamically and shared with the IMD 103, but are not persistently stored and are used for a single patient data exchange. Each crypto key 122 is uniquely assigned to the IMD 103. In one embodiment, the crypto key 103 has a length of 128 bits, is symmetric or is both 128-bits long and symmetric. Other crypto key lengths and symmetries are possible.

The crypto key 122 is used by the IMD 103 and the programmer 123, repeater 124 or other wireless computing device 125 to perform authentication prior to starting a data exchange session. Upon completing authentication, patient information can be sent in the clear or, optionally, in encrypted form, also using the crypto key 122. In one embodiment, the sensitive information to be exchanged is hashed on the sending end with the crypto key 122 to form an original fingerprint. The sensitive information and the original fingerprint are transmitted and the sensitive information is again hashed with the crypto key 122 on the receiving end to form a comparison fingerprint. If the original and comparison fingerprints match, the sensitive information is authenticated.

In the described embodiment, the crypto key 122 serves three functions:

(1) Allows both the IMD 103 and the programmer 123, repeater 124 or other wireless computing device 125 to authenticate individual commands as exchanged during the data exchange session over an RF or other long range wireless link. Authentication ensures that the only commands acted upon are those commands originating from a trusted source.

(2) Allows the IMD 103 and the programmer 123, repeater 124 or other wireless computing device 125 to check the integrity of the sensitive information received over an RF or other long range wireless link. Data integrity checking ensures that the only commands acted upon are those commands that have not been altered, either maliciously or accidentally. In a further embodiment, the IMD 103 verifies the integrity of messages received from a programmer 123, repeater 124 or other wireless computing device 125 and, alternatively, a programmer 123, repeater 124 or other wireless computing device 125 verifies the integrity of messages received from the IMD 103, such as described in commonly-assigned U.S. Pat. No. 7,228,182, to Healy et al., issued Jun. 5, 2007, the disclosure of which is incorporated by reference.

(3) Allows the IMD 103 and the programmer 123, repeater 124 or other wireless computing device 125 to encrypt and decrypt sensitive information, including any PHI, transmitted or received over an RF or other long range wireless link. Encryption allows the sensitive information to be securely transmitted over an RF or other long range wireless link in compliance with applicable patient health information privacy laws and regulations. In a further embodiment, the programmer 123, repeater 124 or other wireless computing device 125 preencrypts sensitive information, including any PHI, which can be stored on an IMD as static data for retrieval by health care providers and for use by the IMD, such as described in commonly-assigned U.S. Patent application Ser. No. 10/801,150, entitled "System And Method For Providing Secure Exchange Of Sensitive Information With An Implantable Medical Device," filed Mar. 15, 2004, pending, the disclosure of which is incorporated by reference.

In one embodiment, individual commands and patient data integrity are authenticated using a standard authentication protocol, such as the Keyed-Hashed Message Authentication protocol (HMAC), and sensitive information is encrypted using a standard encryption protocol, such as the Advanced Encryption Standard protocol (AES). Other authentication and encryption techniques and protocols, as well as other functions relating to the use of the crypto key 122 are possible, including the authentication and encryption techniques and protocols described in commonly-assigned U.S. Pat. No. 7,155,290, to Von Arx et al., issued Dec. 26, 2006, the disclosure of which is incorporated by reference.

Patient Health Information Record

Figure 3:
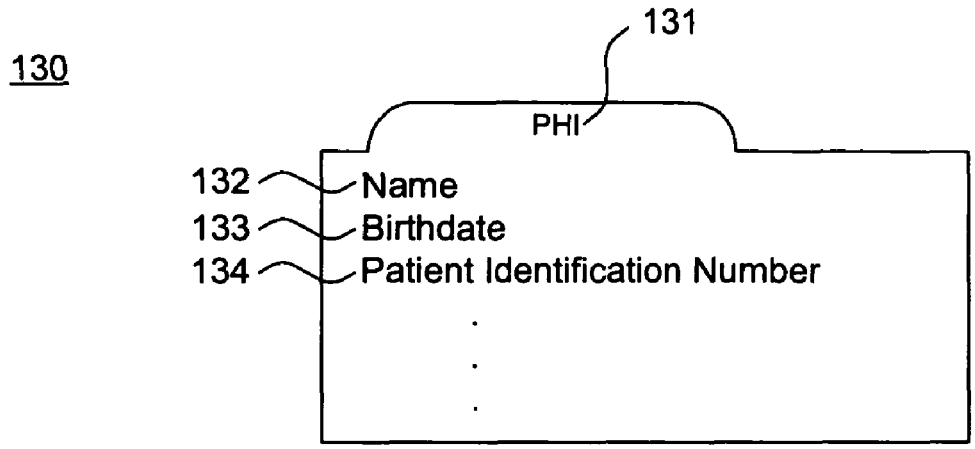
FIG. 3 is a data structure diagram showing a patient health information record.

FIG. 3 is a data structure diagram 130 showing a patient health information (PHI) record 131. At a minimum, patient health information identifies a particular individual to health- and medical-related information. Under HIPAA, there are eighteen categories of patient health information that require protection and include, for example, name 132, birthdate 133, and patient identification number 134. Protectable patient health information can include one or more of the eighteen categories, which can be stored in encrypted form. In addition, each record 131 can also include other types of identifying and treatment profile information, medical history, and other pertinent data. Other types of sensitive information in addition to or in lieu of PHI could also be protectable.

Systems for Securely Authenticating a Data Exchange Session

FIGS. 4A-E are functional block diagrams showing, by way of example, systems for securely authenticating a data exchange session with an implantable medical device, in accordance with embodiments of the present invention. In each system, the crypto key 122 is securely provided to a programmer 123 or repeater 124 through short range inductive telemetry, through a patient designator, through a secure database lookup, using a token, or through a repeater 124, although other means for securely providing the crypto key 122 are possible.

The crypto key 122 is either preprogrammed and persistently stored in the IMD 103 prior to implantation or is generated dynamically by the IMD 103 or by a programmer 123 for subsequent download to the IMD 103 using short range telemetry following implantation. The crypto key 122 is preferably a 128-bit key and can be symmetric or asymmetric.

The IMD 103 includes an on-board RF transceiver (not shown), which interfaces through long range telemetry with a remote RF transceiver. The on-board transceiver is integrated into the IMD 103 with a circumferential antenna wrapping around the external casing of the IMD 103, such as described in commonly-assigned U.S. Pat. No. 6,456,256, to Amundson, issued Sep. 24, 2002, the disclosure which is incorporated by reference. RF communication is performed either by varying the frequency, phase angle or amplitude of the electromagnetic energy radiated by the on-board RF transceiver, such as described in commonly-assigned U.S. Pat. No. 6,574,510, to Von Arx et al., issued Jun. 3, 2003, the disclosure which is incorporated by reference.

Short Range Telemetry

Figure 4A:
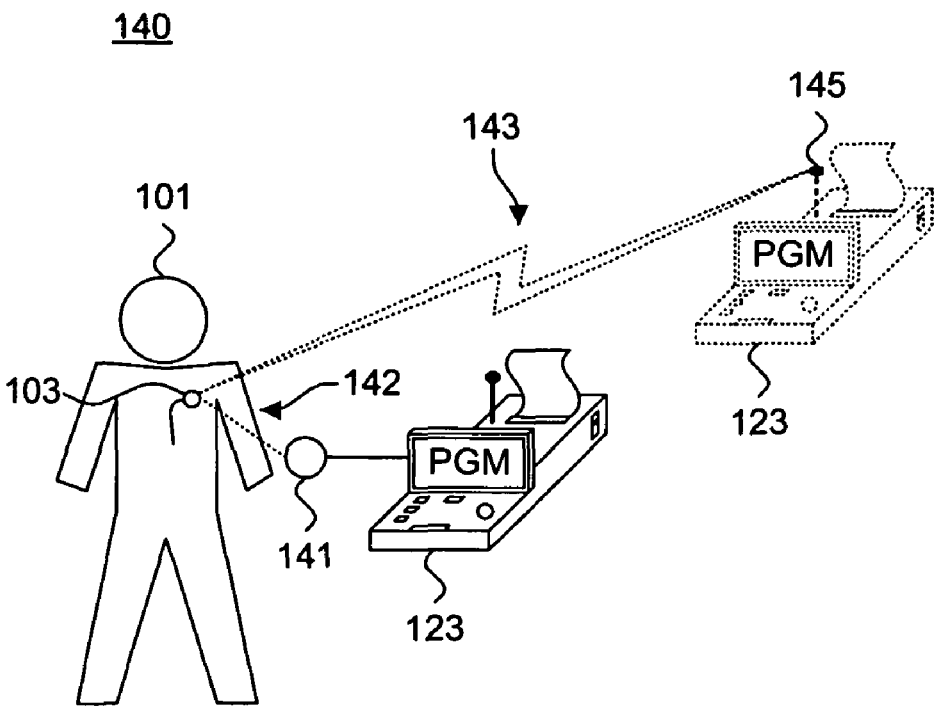
FIGS. 4A-E are functional block diagrams showing, by way of example, systems for securely authenticating a data exchange session with an implantable medical device, in accordance with embodiments of the present invention.

Referring first to FIG. 4A, a system 140 for securely authenticating a data exchange session with an IMD 103 through short range telemetry is shown. Authentication begins with patient/clinician authentication, which is provided through a short range telemetric link 142 between the programmer 123 and IMD 103 using inductive telemetry. A wand 141 is placed over the location of the IM 103, which sends the crypto key 122 to the programmer 123 over the telemetric link 142. The personal interaction between the patient and clinician ensures that patient/clinician authentication is completed.

Upon receiving the crypto key 122, the programmer 123 uses the crypto key 122 to retrieve patient information from the IMD 103 or to send programming interrogating instructions to the IMD 103 over a long range telemetric link 143 using RF telemetry. The ID 103 interfaces to an RF transceiver 145 integral to the programmer 123.

The IMD 103 communicates with the programmer 123 via the wand 141 through short range telemetry. Short range telemetry includes, nonexclusively, inductive telemetry. Data is digitally exchanged between the IMD 103 and the programmer 123 using standard protocols, such as ASK (amplitude shift key), FSK (frequency shift key), PSK (phase shift key) and QPSK (quadrature phase shift key). Signals are inductively exchanged through the wand 141, such as described in commonly-assigned U.S. Pat. No. 4,562,841, to Brockway et al., issued Jan. 2, 1986, the disclosure which is incorporated by reference.

In a further embodiment, patient information is stored in an IMD 103 in unencrypted form. The unencrypted patient information can only be directly retrieved through short range inductive telemetry. However, the IMD 103 can also encrypt the unencrypted patient information for communication through long range telemetry. For instance, the programmer 123 can generate a session crypto key 122, which is communicated to the IMD 103 via short range telemetric signals. The IMD 103 can then use the session crypto key 122 to encrypt and communicate the patient information through long range telemetry.

In a further embodiment, one or more repeaters (not shown) augment the long range telemetric communication by relaying the telemetric signals from the on-board RF transceiver of the IMD 103 to the RF transceiver 145.

Patient Designator

Figure 4B:
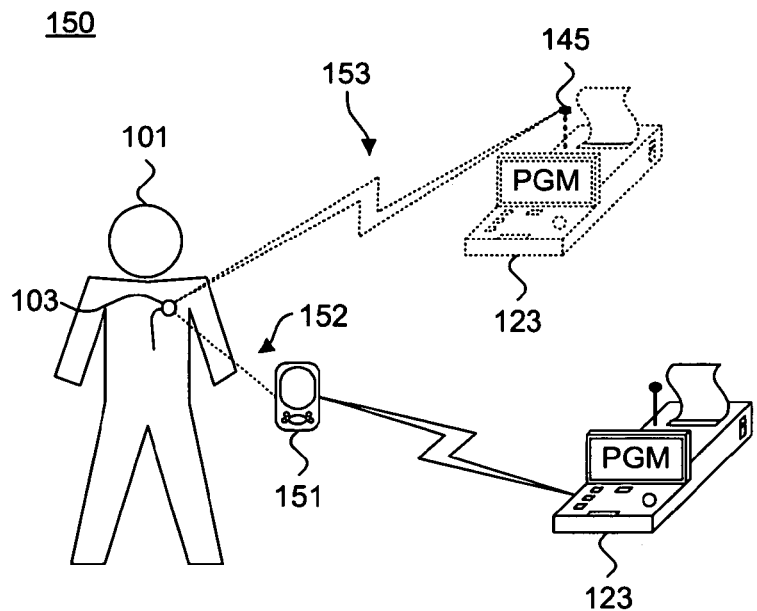

Referring next to FIG. 4B, a system 150 for securely authenticating a data exchange session with an IMD 103 through a patient designator 151 is shown. Authentication begins with patient/clinician authentication, which is provided through a patient designator 151. The patient designator is a battery-powered device that communicates with other devices, such as the IMD 103, through a short range telemetric link 152. Data is digitally exchanged between the IMD 103 and the patient designator 151 using standard protocols, such as ASK, FSK, PSK and QPSK.

In one embodiment, the patient designator 151 retrieves the crypto key 122 from the IMD 103 through the short range telemetric link 152 and provides the retrieved crypto key 122 to the programmer 123. The patient designator 151 interfaces to the programmer 123 through one of several interfaces. First, the patient designator 151 and programmer 123 can interface over a serial connection, such as an RS-232C, USB or IEEE 1394 interface specification. The patient designator 151 and programmer 123 can also interface through an inductive telemetry link. Finally, the patient designator 151 and programmer 123 can interface through a secure wireless encrypted link. Other types of interfacing between the patient designator 151 and programmer 123 are possible.

In a further embodiment, one or more repeaters (not shown) augment the long range telemetric communication by relaying the telemetric signals from the on-board RF transceiver of the IMD 103 to the RF transceiver 145.

In a further embodiment, the patient designator 151 can randomly generate a 128-bit crypto key 122, which is programmed into the IMD 103 using the short range telemetric link 152. The patient designator 151 similarly programs the same crypto key 122 into the programmer 123 using the serial link, short range telemetric link, or secure wireless link.

In a further embodiment, the IMD 103 is preprogrammed with a persistently stored crypto key 122. The patient designator 151 retrieves the crypto key 122 from the IMD 103 via the short range telemetric link 152 and provides the retrieved crypto key 122 to the programmer 123 through a serial link, short range telemetric link, or secure wireless link.

In a further embodiment, the programmer 123 randomly generates a session crypto key 122, which is preprogrammed into the patient designator 151 through the serial link, short range telemetric link, or secure wireless link. The patient designator 151 subsequently programs the session crypto key into the IMD 103 when the clinician initiates the data exchange session possibly at the later time.

Secure Lookup

Figure 4C:
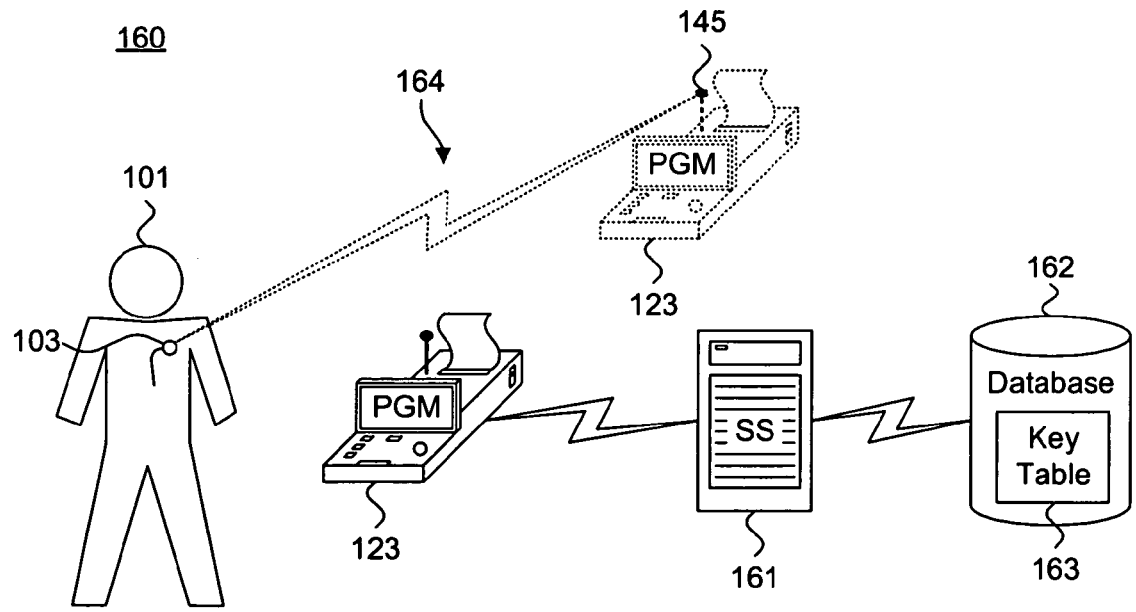

Referring next to FIG. 4C, a system 160 for securely authenticating a data exchange session with an IMD 103 through secure lookup is shown. Authentication begins with patient/clinician authentication through a secure lookup. The IMD 103 is preprogrammed with a persistently stored crypto key 122. The crypto key 122 is also stored in a secure database 162, which contains a key table 163 associating the crypto key 122 with the IMD 103 and a list of authorized clinicians and passwords. The clinician accesses the secure database 162 through a secure server 161 and retrieves the crypto key 122 from the key table 163 upon successful authentication. The programmer 123 interfaces to the secure server 161 through a secure connection, such as provided through a Secure Socket Layer (SSL) or Internet Protocol security (IPSec). In a further embodiment, the programmer 123 interfaces to the secure server 161 through a dedicated serial or hardwired connection.

Token

Figure 4D:
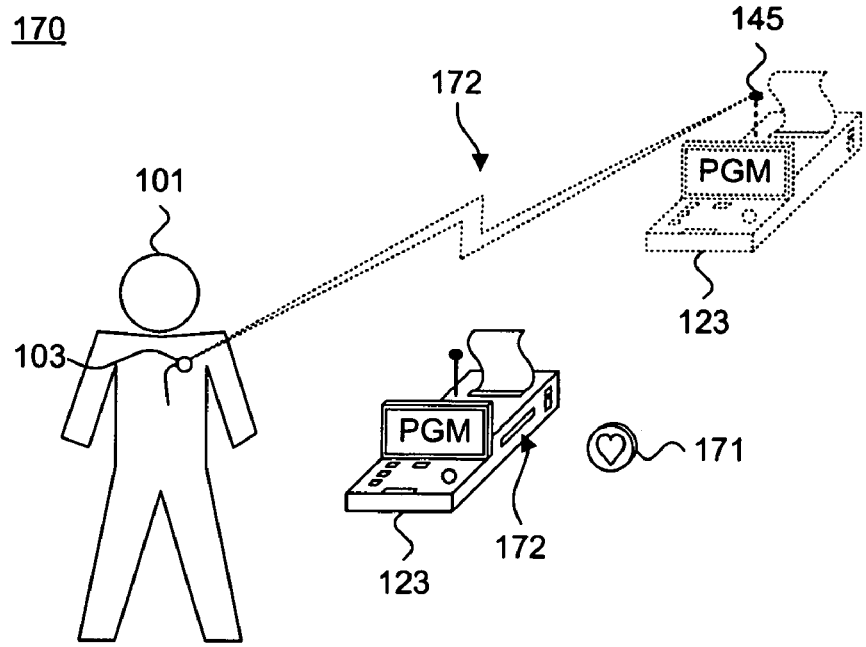

Referring next to FIG. 4D, a system 170 for securely authenticating a data exchange session with an IMD 103 using a token 171 is shown. Authentication begins with patient/clinician authentication using a physical token 171. The physical token 171 records the crypto key 122 either through a physical label, such as alphanumeric text, bar coding or other outwardly-appearing indications, or through internal storage, such as through a transistor, memory circuit, or other form of electronically or magnetically readable storage medium. Outwardly, the physical token 171 can be in the form of wearable jewelry, such as a bracelet, pendant or coin; wallet-sized card, such as SmartCard or barcode card; and other physical forms.

The IMD 103 is preprogrammed with a persistently stored crypto key 122, which is also stored on the physical token 171, which is provided to the patient or clinic. Prior to initiating a data exchange session, the crypto key 122 is retrieved from the physical token 171 by reading the physical token 171 using, for instance, a reader 172 provided on the programmer 123. In one embodiment, the programmer 123 reads the physical token 171 through short range telemetry. In a further embodiment, the physical token 171 includes a barcode, which is read by the programmer 123 optically. An example of a barcode reader suitable for use in the programmer 123 is the intelliScaner 5000XL, manufactured by Intelli Innovations, Inc., Cary, N.C. In a further embodiment, the physical token 171 includes a transistor or similar electronic component and the crypto key 122 is retrieved from the physical token 171 electronically or magnetically. In a further embodiment, the physical token 171 includes solid state componentry for persistently storing the crypto key 122 and the programmer 123 retrieves the crypto key 122 through a serial interface connection. In a further embodiment, the crypto key 122 is manually entered into the programmer 123 after being physically read from the physical token 171.

Repeater

Figure 4E:
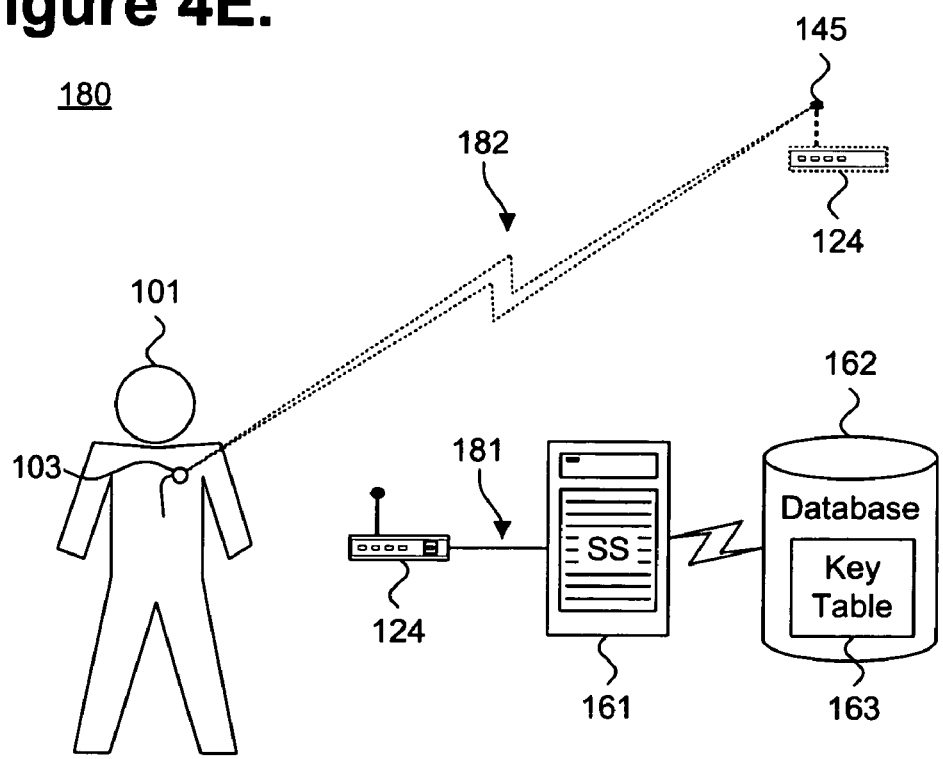

Referring finally to FIG. 4E, a system 180 for securely authenticating a data exchange session with an IMD 103 through a repeater 124 is shown. Authentication begins with patient/clinician authentication. In one embodiment (not shown), the IMD 103 and a repeater 124 are both preprogrammed with the same persistent crypto key 122, such as during the manufacturing process. This form of patient/clinician authentication takes advantage of the assignment of a specific repeater 124 to a unique IMD 103 for an individual patient, thereby allowing the repeater 124 to be preprogrammed with the crypto key 122.

In a further embodiment, the crypto key 122 assigned to the IMD 103 is stored in a key table 163 maintained in a secure database 162. The crypto key 122 is retrieved from the secure database 162 by a repeater 124 following authentication with a secure server 161. Only an authorized factory-provided repeater 161 can receive a copy of the crypto key 122, thereby ensuring patient/clinician authentication.

In a still further embodiment (not shown), the crypto key 122 is retrieved from the IMD 103 by the programmer 123 through short range telemetry in a manner analogous to patient/clinician authentication provided through a patient designator 151, as further described above with reference to FIG. 4B. Thus, the programmer 123 retrieves the crypto key 122 from the IMD 103 through a short range telemetric link and provides the crypto key 122 to the repeater 124 through a serial connection, short range telemetric link, secure wireless connection, or other similar interface.

Secured Area Definition

Figure 5:
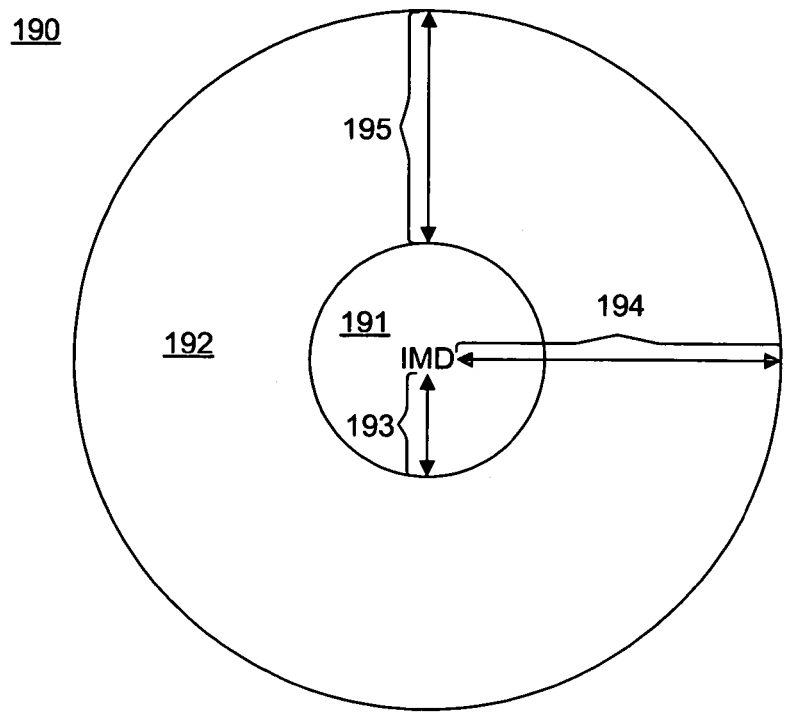
FIG. 5 is a block diagram showing, by way of example, a secure area defined around an IMD.

FIG. 5 is a block diagram 190 showing, by way of example, a secured area defined around an IMD 103. Patient/clinician authentication can only be transacted within a logically defined secured area 191, whereas data exchange session can be transacted in a logically defined non-secured area 192, provided patient/clinician authentication is successfully completed and all patient information exchanged is properly encrypted.

The range 193 of the secured area 191 is based on the form of patient/clinician authentication transacted. For example, short range inductive telemetry has a range 193 of about six centimeters. The range of the non-secured area 194 similarly depends on the form of long range telemetry used. For RF telemetry, the range 194 can be 20 or more feet from the patient, depending on patient orientation relative to the programmer 123 or repeater 124. The use of encryption enables the range 193 of the secured area 191 to have an extended range 195 provided by the non-secured area 192 through encryption or authentication.

Method Overview

Figure 6:
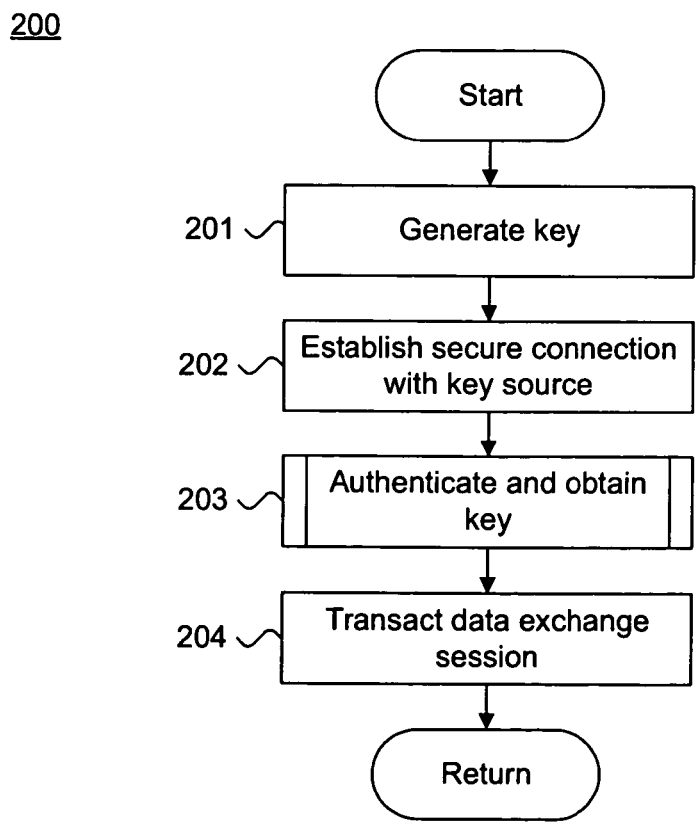
FIG. 6 is a flow diagram showing a method for securely authenticating a data exchange session with an implantable medical device, in accordance with embodiments of the present invention.

FIG. 6 is a flow diagram showing a method 200 for securely authenticating a data exchange session with an IMD 103, in accordance with embodiments of the present invention. The method 200 is described as a sequence of process operations or steps, which can be executed, for instance, by the programmer 123, repeater 124, or other components. The operations are performed by various components in each of the embodiments through short range telemetry, a patient designator, secure lookup, using a physical token, and a repeater to provide patent/clinician authentication.

Initially, the crypto key 122 is generated (block 201). Depending upon the system, the crypto key 122 could be generated dynamically by a programmer 123 or, if applicable, the repeater 124, for subsequent download to the IMD 103 using short range telemetry following implantation. Similarly, the crypto key 122 could be generated during the manufacturing process and persistently stored in the IMD 103 prior to implantation. Alternatively, the crypto key 122 could be dynamically generated by the IMD 103. The systems using secure lookup and a physical token can only operate with a persistently stored crypto key 122, since the crypto key 122 is securely provided through means external to and independent from the IMD 103. The systems using short range telemetry, a patient designator, and a repeater can operate with either a persistently stored crypto key 122 or a dynamically generated crypto key 122.

Next, a secure connection is established with the source of the crypto key 122 (block 202). The form of the secure connection is dependent upon the type of key source. For instance, if the key source is the IMD 103, the secure connection could be established through inductive telemetric link. If the key source is the key table 163 in the secure database 162, the secure connection could be established through a dedicated serial or hardwired connection or through a logically secure network connection, such as provided through SSL or IPSec, to the secure server 161. Similarly, if the key source is a physical token 171, the secure connection could be established through a reader 172 or similar physical information retrieval mechanism, such as optical, magnetic, SmartCard, and the short range telemetric link. Finally, if the key source is a repeater 124, the secure connection could be established through an interface compatible with the repeater 124, such as through inductive or magnetic telemetry or a dedicated serial or hardwired connection.

The crypto key 122 is authenticated and obtained (block 203), as further described below with reference to FIGS. 7-11. Finally, the data exchange session is transacted (block 204), between the IMD 103 and the programmer 123 or repeater 124. The method then terminates.

Short Range Telemetry

Figure 7:
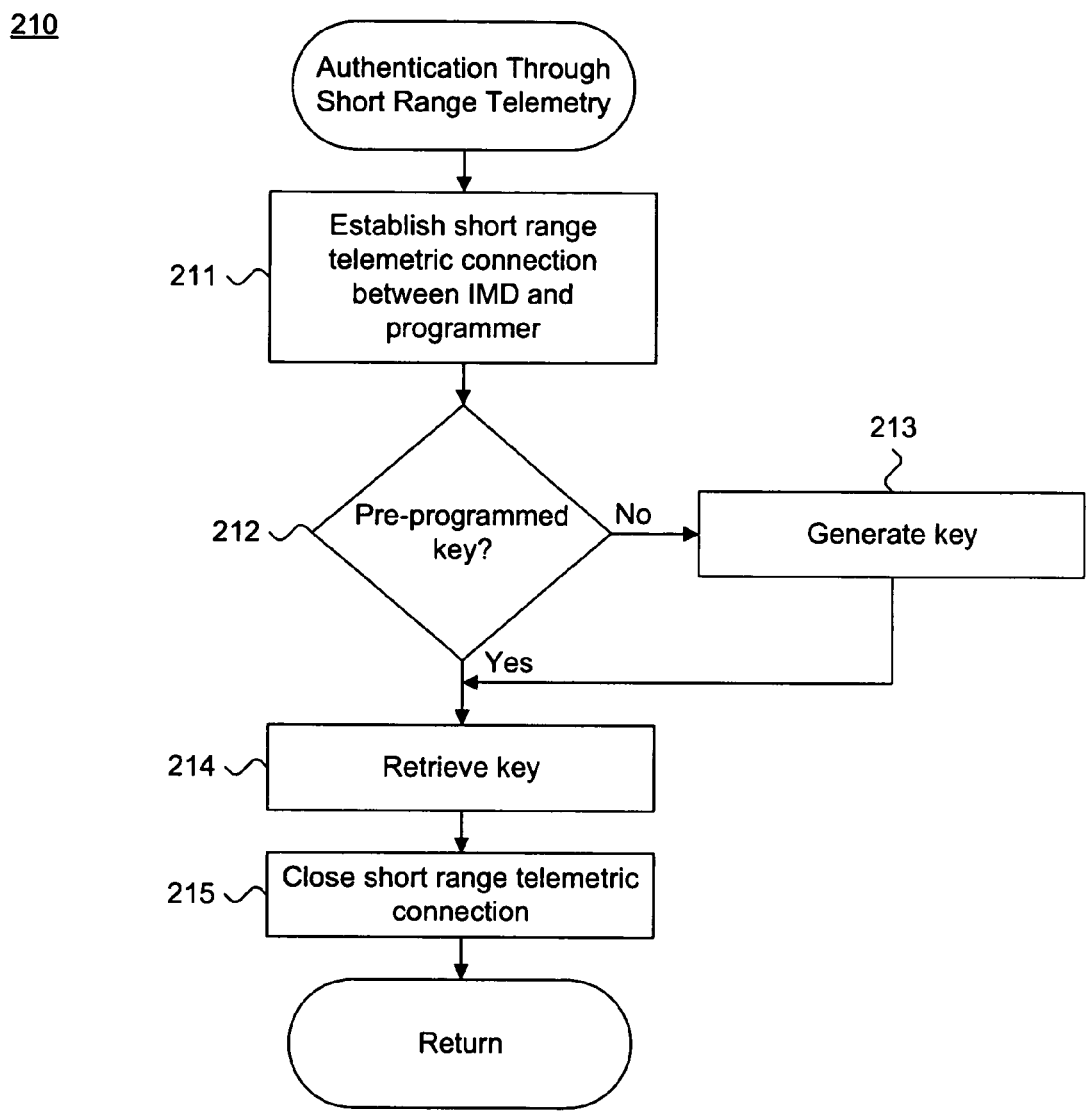
FIG. 7 is a flow diagram showing a routine for performing crypto key authentication through short range telemetry, in accordance with one embodiment.

FIG. 7 is a flow diagram 210 showing a routine for performing crypto key authentication through short range telemetry, in accordance with one embodiment. The purpose of this routine is to securely retrieve the crypto key 122 directly from the IMD 103 through inductive or magnetic telemetry using a programmer 123.

A short range telemetry connection is established between the IMD 103 and the programmer 123 (block 211). If the crypto key 122 is pre-programmed, that is, persistently stored on the IMD 103 (block 212), the crypto key 122 is retrieved from the IMD 103 (block 214) over the short range telemetric link. Otherwise, if the crypto key 122 is not pre-programmed (block 212), the IMD 103 generates the crypto key 122 (block 213), which is then retrieved by the programmer 123 (block 214). In a further embodiment, the programmer 123 dynamically generates the crypto key 122, which is downloaded to the IMD 103. Upon the successful retrieval of the crypto key from IMD 103, the short range telemetric connection is closed (block 215) and the routine returns.

Patient Designator

Figure 8:
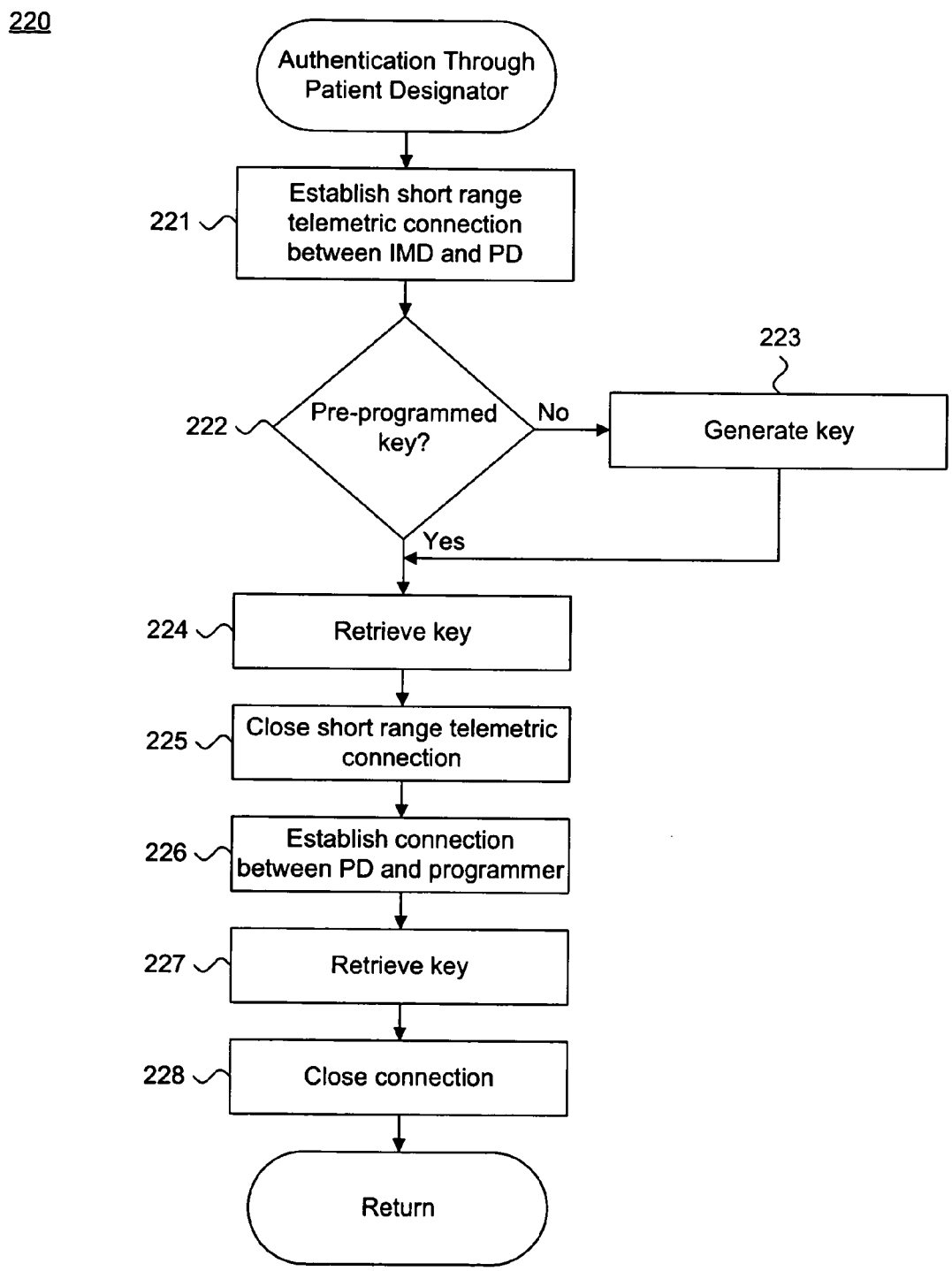
FIG. 8 is a flow diagram showing a routine for performing crypto key authentication through a patient designator, in accordance with one embodiment.

FIG. 8 is a flow diagram showing a routine 220 for performing crypto key authentication through a patient designator 151, in accordance with one embodiment. The purpose of this routine is to securely retrieve the crypto key 122 directly from the IMD 103 through inductive or magnetic telemetry using a patient designator 151.

A short range telemetric connection is established between the IMD 103 and the patient designator 151 (block 221). If the crypto key 122 is pre-programmed, that is, persistently stored on the IMD 103 (block 222), the crypto key 122 is retrieved from the IMD 103 (block 224) over the short range telemetric link. Otherwise, if the crypto key 122 is not pre-programmed (block 222), the IMD 103 or programmer 123 generates the crypto key 122 (block 223), which is then retrieved by the patient designator 151 (block 224). In a further embodiment, the programmer 123 dynamically generates the crypto key 122, which is downloaded to the IMD 103 and the patient designator 151. Upon the successful retrieval of the crypto key from ID 103, the short range telemetric connection is closed (block 225).

A connection is then established between the patient designator 151 and the programmer 123 (block 226). The connection can be through a serial, a short range telemetric, a secure encrypted wireless, or other form of secure connection. The crypto key 122 is retrieved by the programmer 123 from the patient designator 151 (block 227) and the connection is closed (block 228). The routine then returns.

Secure Lookup

Figure 9:
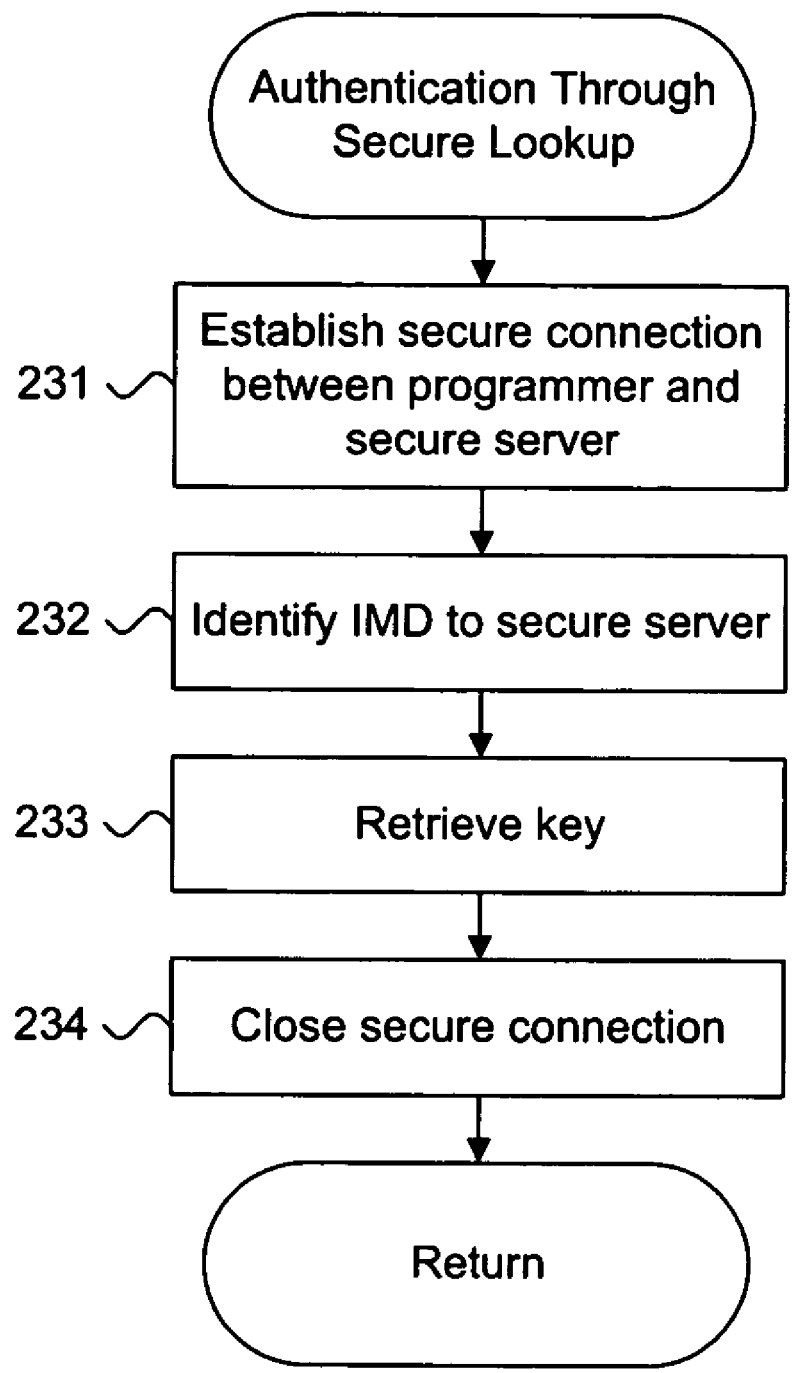
FIG. 9 is a flow diagram showing a routine for performing crypto key authentication through a secure lookup, in accordance with one embodiment.

FIG. 9 is a flow diagram showing a routine 230 for performing crypto key authentication through a secure lookup, in accordance with one embodiment. One purpose of this routine is to retrieve a crypto key 122 matching a crypto key 122 pre-programmed and persistently stored in an IMD 103, as chronicled in a secure database 162.

A secure connection is established between the programmer 123 and the secure server 161 to provide access to the secure database 162 (block 231). The secure connection can be through a dedicated serial or hardwired connection or through a secure remote network connection. The IMD 103 is identified to the secure server 161 and appropriate authentication of the requesting programmer 123 is completed (block 232). The crypto key 122 is then retrieved from the key table 163 (block 233) and the secure connection is closed (block 234). The routine then returns.

Token

Figure 10:
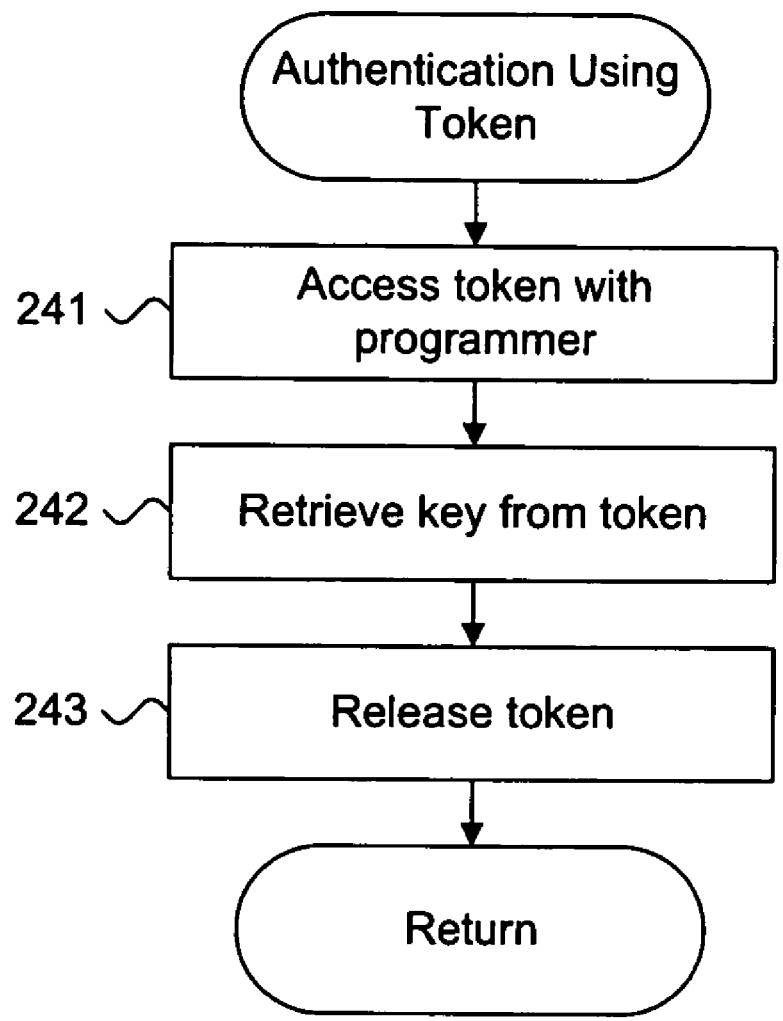
FIG. 10 is a flow diagram showing a routine for performing crypto key authentication using a physical token, in accordance with one embodiment.

FIG. 10 is a flow diagram showing a routine 240 for performing crypto key authentication using a physical token 171, in accordance with one embodiment. One purpose of this routine is to retrieve a crypto key 122 from a physical token 171 based on the form of the physical token 171 employed.

The programmer 123 accesses the physical token 171 (block 241) based on the form of the crypto key recordation and the crypto key 122 is then retrieved from the physical token 171 (block 242). For instance, if the crypto key 122 is stored magnetically on the physical token 171, the programmer 123 electronically retrieves the crypto key 122 from the physical token 171. Similarly, if the crypto key 122 is printed as a barcode, the programmer 123 optically reads the crypto key 122 from the physical token 171. As well, if the physical token 171 is a SmartCard, the crypto key 122 is read from the SmartCard as the physical token 171 is slid through a SmartCard reader. The physical token 171 is then released following crypto key retrieval (block 243) and the routine returns.

Repeater

Figure 11:
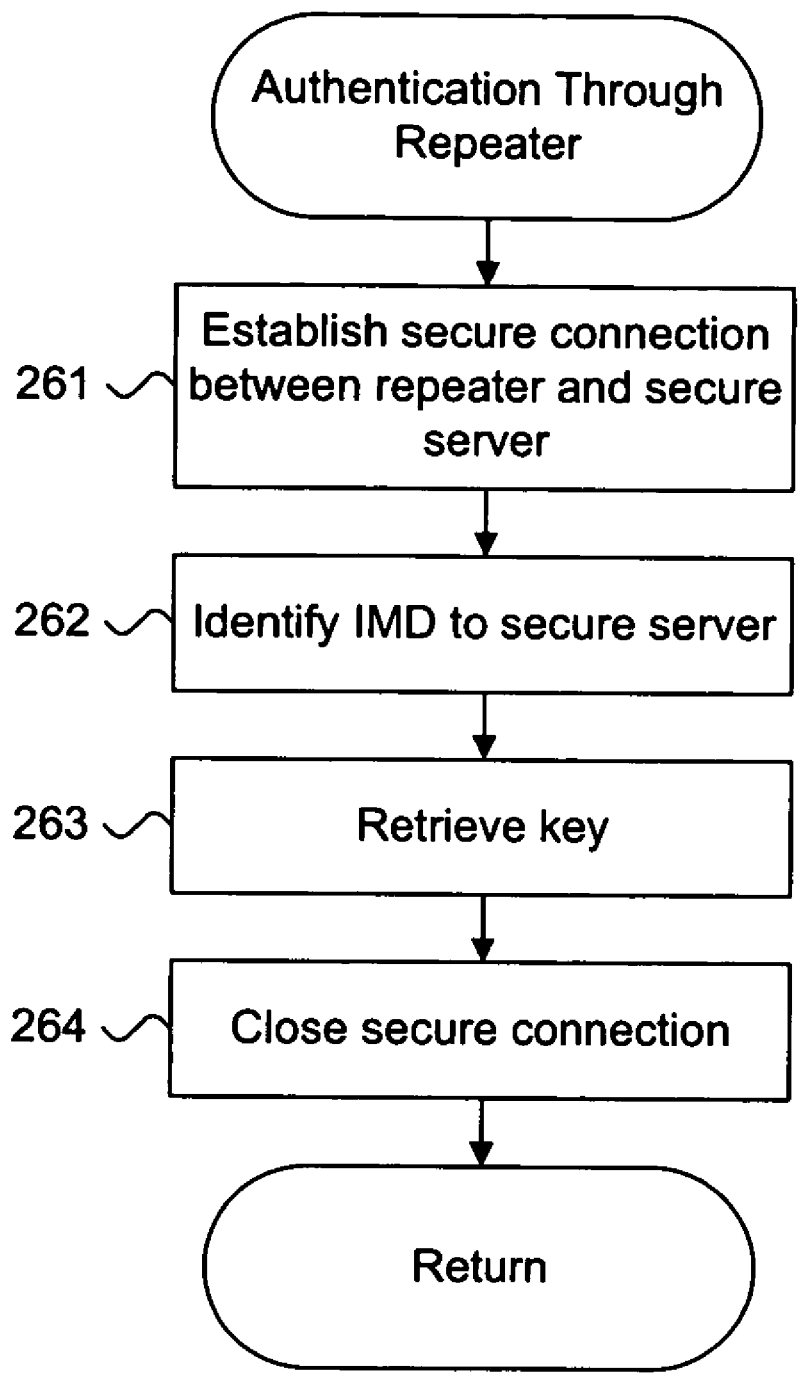
FIG. 11 is a flow diagram showing a routine for performing crypto key authentication through a secure lookup with a repeater, in accordance with one embodiment.

FIG. 11 is a flow diagram showing a routine 250 for performing crypto key authentication through a secure lookup with a repeater 124, in accordance with one embodiment. One purpose of this routine is to retrieve a crypto key 122 matching a crypto key 122 pre-programmed and persistently stored in an IMD 103, as chronicled in a secure database 162.

A secure connection is established between the repeater 124 and the secure server 161 to provide access to the secure database 162 (block 261). The secure connection can be through a dedicated serial or hardwired connection or through a secure remote network connection. The IMD 103 is identified to the secure server 161 and appropriate authentication of the requesting repeater 124 is completed (block 262). The crypto key 122 is then retrieved from the key table 163 (block 263) and the secure connection is closed (block 264). The routine then returns.

In a further embodiment (not shown), the IMD 103 and a repeater 124 are both preprogrammed with the same persistent crypto key 122, such as during the manufacturing process. In a still further embodiment (not shown), the crypto key 122 is retrieved from the IMD 103 by the programmer 123 through short range telemetry in a manner analogous to patient/clinician authentication provided through a patient designator 151, as further described above with reference to FIG. 8.

While the invention has been particularly shown and described as referenced to the embodiments thereof, those skilled in the art will understand that the foregoing and other changes in form and detail may be made therein without departing from the spirit and scope of the invention.

What is claimed is:

1. An apparatus for securely authenticating a data exchange session with an implantable medical device, comprising:
    an external device comprising a key generator configured to dynamically generate a crypto key for each data exchange session with an implantable medical device;
    the external device configured to establish an inductive telemetric link to the implantable medical device and to download the crypto key to the implantable medical device through the inductive telemetric link for each data exchange session;
    the external device configured to then transact the data exchange session with the implantable medical device through a long range telemetric link authenticated with the crypto key.

2. An apparatus according to claim 1, further comprising:
    an authentication component configured to employ the crypto key during the data exchange session, comprising at least one of:
        a command authenticator configured to authenticate commands exchanged through the external device with the implantable medical device and;
        a data integrity checker configured to check the integrity of the data received by and transmitted from the external device; and
        a data encrypter configured to encrypt the data received by and transmitted from the external device.

3. An apparatus according to claim 1, wherein the external device comprises a programmer.

4. An apparatus according to claim 3, wherein the crypto key is provided from the programmer to a repeater.

5. An apparatus according to claim 1, wherein the external device comprises a patient designator.

6. An apparatus according to claim 1, wherein the crypto key comprises at least one of a 128-bit crypto key and a symmetric crypto key.

7. An apparatus according to claim 1, wherein the implantable medical device comprises at least one of an implantable cardiac device, neural stimulation device, and drug therapy dispensing device.

8. An apparatus according to claim 1, wherein the implantable medical device maintains patient health information in an encrypted form.

9. An apparatus according to claim 1, wherein the implantable medical device maintains patient health information in an unencrypted form and is accessible in the unencrypted form exclusively through a short range telemetric connection.

10. An apparatus according to claim 1, wherein the long range interface is augmented using one or more repeaters.

* * * * *